US009233090B2

(12) United States Patent
Breuille et al.

(10) Patent No.: US 9,233,090 B2
(45) Date of Patent: Jan. 12, 2016

(54) CYSTEINE AND FOOD INTAKE

(75) Inventors: Denis Breuille, Lausanne (CH); Isabelle Papet, Clermont-Ferrand (FR); Karine Vidal, Lausanne (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 13/880,923

(22) PCT Filed: Oct. 19, 2011

(86) PCT No.: PCT/EP2011/068231
§ 371 (c)(1),
(2), (4) Date: Apr. 22, 2013

(87) PCT Pub. No.: WO2012/052463
PCT Pub. Date: Apr. 26, 2012

(65) Prior Publication Data
US 2013/0225486 A1    Aug. 29, 2013

(30) Foreign Application Priority Data
Oct. 21, 2010  (EP) .................................... 10188399

(51) Int. Cl.
*A61K 31/198*    (2006.01)
*A23L 1/305*    (2006.01)

(52) U.S. Cl.
CPC ............. *A61K 31/198* (2013.01); *A23L 1/3051* (2013.01)

(58) Field of Classification Search
None
See application file for complete search history.

(56) References Cited

U.S. PATENT DOCUMENTS

| 4,665,082 | A | 5/1987 | Meister et al. |
| 5,627,152 | A | 5/1997 | Kenyhercz et al. |
| 2004/0047896 | A1* | 3/2004 | Malnoe et al. ................ 424/439 |
| 2005/0153019 | A1 | 7/2005 | Fuchs et al. |
| 2005/0215640 | A1 | 9/2005 | Baxter et al. |
| 2007/0286909 | A1 | 12/2007 | Smith et al. |
| 2009/0324518 | A1 | 12/2009 | Korth |

FOREIGN PATENT DOCUMENTS

| JP | S62286923 | 12/1987 |
| JP | H05294833 | 11/1993 |
| JP | 2009001507 | 1/2009 |
| RO | 119122 | 4/2004 |
| WO | 9302682 | 2/1993 |
| WO | WO 02/15720 A2 * | 2/2002 ................ A23L 1/30 |
| WO | WO0215720 | 2/2002 |
| WO | 2009157759 | 12/2009 |
| WO | 2010028503 | 3/2010 |

OTHER PUBLICATIONS

Chandan et al ("Manufacturing Yogurt and Fermented Milks" (2006) Blackwell Publishing).*
Bounous et al ("The biological activity of undenatured dietary whey proteins: role of glutathione" (Aug. 1991) Clin Invest Med 14(4): 296-309).*
Livestrong ("Cysteine in Eggs" http://www.livestrong.com/article/283026-cysteine-in-eggs/ (2014) downloaded Apr. 8, 2014).*
Hack et al (FASEB (Jan. 1997) 11: 84-92).*
Aqua Calc (http://www.aqua-calc.com/page/density-table/substance/egg-coma-and-blank-yolk-coma-and-blank-raw-coma-and-blank-fresh, downloaded May 21, 2014).*
Fullness Factor (https://web.archive.org/web/20100713172702/http://nutritiondata.self.com/topics/fullness-factor (Jul. 13, 2010) downloaded May 21, 2014).*
Livestrong ("Cysteine in Eggs" http://www.livestrong.com.article1283026-cysteine-in-eggs/(2014) downloaded Apr. 8, 2014).*
Derocha (http://www.ahealthiermichigan.org/2011/10/11/the-nurtional-value-of-egg-whites-versus-egg-yolks-what-do-you-use/ (Oct. 11, 2011) downloaded Apr. 8, 2014).*
Hack et al (FASEB (Jan. 1997) 11 : 84-92).*
Aqua Calc (http://www.aqua-calc.com/page/density-table/substance/egg . . . ), downloaded May 21, 2014).*
Bridge (2006 Research) (http://www.babs.unsw.edu.au/research/antioxidants-gamma-glutamylcysteine, downloaded May 21, 2014).*
Seiler (Nutrition (2001) 17: 496-498).*
Calorie Count (http://caloriecount.about.com/calories-eggnog-i1057, downloaded May 21, 2014).*
Thesaurus.com (Definition of "Pure" downloaded from on Jan. 30, 2015 from http://www.thesaurus.com/browse/pure).*
Mbodji, K., et al. "P233 Effect of a New Oral Supplement Enriched in Cysteine on Nutritional Status of Stressed Rats." Clinical Nutrition Supplements 4.2 (2009), p. 123.
Search Report for International Patent Application No. PCT/EP2001/068231 mailed Nov. 30, 2011.
Written Opinion for International Patent Application No. PCT/EP2001/068231 mailed Nov. 30, 2011.
European Office Action 11770786.9 dated Apr. 2, 2014, 4 pages.
European Patent Office Communication for Application No. 11770786.9-1460, dated Jan. 30, 2015, 3 pages.
Japanese Office Action for Application No. P2013-534304, Dispatch No. 367485, dated Aug. 18, 2015, 8 pages.

* cited by examiner

*Primary Examiner* — Marcela M Cordero Garcia
*Assistant Examiner* — Mindy Newman
(74) *Attorney, Agent, or Firm* — K&L Gates LLP

(57) ABSTRACT

The present invention relates to the field of nutrition; in particular to the prevention and/or treatment of malnutrition. One embodiment of the present invention relates to a nutritional composition enriched in cysteine for use in the treatment and/or prevention of malnutrition and disorders related thereto. Such a composition may in particular, but not exclusively, be useful for the elderly population.

27 Claims, 4 Drawing Sheets

CYSTEINE AND FOOD INTAKE

CROSS REFERENCE TO RELATED APPLICATIONS

The present application is a National Stage of International Application No. PCT/EP2011/068231, filed on Oct. 19, 2011, which claims priority to European Patent Application No. 10188399.9, filed Oct. 21, 2010, the entire contents of which are being incorporated herein by reference.

The present invention relates to the field of nutrition; in particular to the prevention and/or treatment of malnutrition. One embodiment of the present invention relates to a nutritional composition enriched in cysteine for use in the treatment or prevention of malnutrition and disorders related thereto. Such a composition may in particular, but not exclusively, be useful for the elderly population.

Anorexia is the decreased sensation of appetite. Many possible causes exist for a decreased appetite, some of which may indicate a serious clinical condition, or pose a significant risk. Oftentimes anorexia is a consequence of other illnesses. Under such circumstances malnutrition is a significant problem since it will delay the recovery process and may even prevent a full recovery.

Anorexia is often present in the ageing population. Despite the increase in body fat and obesity that occurs with aging, there is a linear decrease in food intake over the life span. This may be explained by decreased physical activity and an altered metabolism with aging. Ageing-associated anorexia may have substantial adverse effects. The age-associated physiologic reduction in appetite and food intake has been termed "the anorexia of aging". 'Physiological' anorexia and weight loss of ageing predispose to pathological weight loss and malnutrition. This physiologic anorexia is caused for example by an altered hormonal and neurotransmitter regulation of food intake. Marked weight loss in the elderly drives morbidity and increased mortality, has a negative impact on the quality of life and contributes to frailty.

Today, anorexia is often treated by administration of a variety of medicaments, some of which may have unwanted side effects.

Consequently, there is a need in the art for a natural way to treat and/or prevent malnutrition and disorders related thereto without unwanted side effects, in particular in the elderly. Ideally, this should be accomplished by a composition that is available to everyone, is liked by the consumers and can be used on a daily basis.

The present inventors have addressed this need.

Hence, it was the object of the present invention to improve the state of the art and to provide the art with a composition that achieves the object of the present invention.

The inventors were surprised to see that they could achieve this object by the subject matter of the independent claim. The dependant claims further develop the idea of the present invention.

In particular the inventors have found that cysteine can be used, e.g. as part of a composition for enteral nutrition or a food product, to maintain or improve food intake, for example in the elderly.

The inventors found that cysteine exhibits an anti-anorexic property, for example an anti ageing-associated anorexia property. Such effect was not observed with alanine-supplemented diet (control diet). To the inventor's best knowledge, this is the first description of a beneficial effect of cysteine on food intake. Consequently, providing cysteine-rich diet or adding cysteine to a food product, for example in a quantity higher than the normal requirement would allow counteracting the decrease in food consumption that occurs, e.g., in the elderly. There are also many health-related conditions are associated with anorexia, e.g. chemotherapy, infection, anorexia nervosa, or stress conditions. Also here cysteine may be used to treat or prevent anorexia and related conditions. Hence, cysteine may also be used in clinical products to control food intake, for example.

Consequently, one embodiment of the present invention is a nutritional composition enriched in cysteine.

"Enriched" in cysteine means that cysteine was either added to a nutritional composition or that a food composition is treated in a way that its natural cysteine content per gram is increased. A composition is further considered "enriched" in cysteine if the composition contains cysteine in an amount that exceeds the recommended daily intake (RDI). The recommended daily intake for cysteine for infants (0-12 months) is 45 mg/kg body weight; for children (1-17 years) 22 mg/kg body weight; and for adults ($\geq 18$ years) 10 mg/kg body weight.

Cysteine may also be provided in the form of a cysteine precursor selected from the group consisting of cysteine bound in a protein or a peptide hydrolysate or a peptide, for example gamma-glutamyl-cysteine, or an ther form of peptide, for example gamma-glutamyl-cysteine ester, mixed disulfides such as L-cysteine-glutathione cysteine prodrugs, N-acetyl-cysteine (free form, amide or ester forms), S-allyl-cysteine, S-methyl-cysteine, S-ethyl-cysteine, S-propyl-cysteine, TCA (thiazelidineScarboxylic acid), OTC (L-2-Oxothiazolidine-4-carboxylate), bucillamine glutathione and glutathione esters (monomethyl, monoethyl, diethyl, isopropyl), glutathione prodrugs, S-acetyl-glutathione, S-pheylacetate-glutathione, and S-hydroxy-methyl mercapto L-cysteine.

The composition of the present invention may be for use in the treatment and/or prevention of malnutrition and/or disorders related thereto.

The present invention also relates to the use of cysteine for the preparation of a composition to treat and/or prevent malnutrition and/or disorders related thereto.

The composition of the present invention may be additionally or alternatively for use in increasing food intake.

It may also be used for decreasing satiety and/or satiation.

Notably, the inventors found that the administration of the composition of the present invention allowed to significantly increase food intake. Hence, the composition of the present invention may also be used for increasing appetite.

The composition of the present invention allows increasing the willingness to eat as well as the total quantity of ingested food.

Hence, e.g., any disorder related to malnutrition may be treated by administration of the composition of the present invention. For example, the disorder related to malnutrition may be selected from the group consisting of anorexia, anorexia nervosa, cachexia, inflammatory diseases associated with decreased food intake, or combinations thereof.

Low-grade inflammation appears to be an important parameter in the development of the homeosteny, for example associated with ageing. Age-associated low-grade inflammation may cause an increase mortality and morbidity, such as body weight loss. The present invention provides a new nutritional strategy to counterbalance such negative effects of low-grade inflammation that may occur in the elderly, for example.

In one embodiment of the present invention, the composition may be to be administered to the elderly.

A subject is considered as "elderly" or "aged" if it has surpassed the first half of its average expected lifespan in its country of origin, preferably, if it has surpassed the first two thirds of the average expected lifespan in its country of origin, more preferably if it has surpassed the first three quarters of the average expected lifespan in its country of origin, most preferred if it has surpassed the first four fifths of the average expected lifespan in its country of origin.

For example, the composition of the present invention may be to be administered to a person at the age of at least 50 years, at least 60 years, at least 70 years or at least 80 years.

The composition of the present invention may also be to be administered to pets, for example aged pets.

The composition in accordance with the present invention may be for use in the treatment or prevention of an age related decrease in food intake.

The compositions of the present invention will typically contain a protein fraction, a lipid fraction and a carbohydrate fraction.

The protein fraction may comprise at least 3.0 weight-%, at least 4 weight-%, at least 5 weight-%, at least 7 weight-% or at least 10 weight-% cysteine.

In case a subject suffers from an impaired functioning of the gastro-intestinal tract, it may be preferred if for example at least in part a protein source is used that is pre-hydrolyzed.

For the same reason it might be preferred if a lipid source containing MCT (medium chain triglycerides) is used. MCTs have the advantage that they are easily absorbed by the body.

In the framework of the present invention cysteine may typically be administered in a daily dose in the range of about 0.03 to 0.15 g/kg body weight, for example 0.05 to 0.12 g/kg body weight.

In order to achieve such daily doses, the composition may contain cysteine in an amount of at least 2 g/kg dry weight, at least 4 g/kg dry weight, at least 6 g/kg dry weight, at least 8 g/kg dry weight, or at least 10 g/kg dry weight.

Cysteine from any source may be used in the framework of the present invention. Chemically pure cysteine has the advantage of being available in high purity and concentrations allowing a very precise dosing.

However, cysteine may also be provided from natural sources. For example, cysteine may be provided from animal sources such as pork, sausage meat, chicken, turkey, duck, luncheon meat, eggs, milk, milk proteins, whey protein, ricotta, cottage cheese, and/or yogurt; and/or from vegan sources such as red peppers, garlic, onions, broccoli, Brussels sprouts, oats, granola, and/or wheat germ.

These natural sources allow producing natural and effective food compositions without adding artificially produced compounds. It is also possible to meet specific dietary needs, such as for example for vegetarians or vegans.

The compositions of the present invention may have a caloric density of at least 0.5 kcal/g dry weight. Some people with an overall low food intake have problems to digest high caloric food. For such people low caloric formulations are preferred. Otherwise, increasing food intake has a more pronounced effect if food with a higher caloric density is consumed. Hence, the compositions of the present invention may also have a caloric density of at least 0.8 kcal/g dry weight, at least 1.0 kcal/g dry weight, at least 1.5 kcal/g dry weight, or at least 2.0 kcal/g dry weight.

Typically, about 10 to 40% of the calories of the composition may be from proteins. As in particularly elderly people often suffer from insufficient protein intake it may be preferred if about 20 to 40% of the calories of the composition are from proteins.

The composition may also comprise about 15 to 45% of the calories of the composition from lipids, and/or about 20 to 70% of the calories of the composition from carbohydrates.

The composition may be any kind of composition that is acceptable for human or animal consumption. For example, the composition may be selected from the group consisting of a food product, a pet food product, a drink, a pharmaceutical, a nutritional formula, a composition for clinical nutrition, a nutritional powder to be reconstituted by addition of water, a juice or milk, a nutraceutical, a food additive, a food supplement, a dairy product, or a gel.

Food additive or medicaments may be in the form of tablets, capsules, pastilles or a liquid for example.

The compositions may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents, gel forming agents, antioxidants and antimicrobials.

They may also contain conventional pharmaceutical additives and adjuvants, excipients and diluents, including, but not limited to, water, gelatine of any origin, vegetable gums, ligninsulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like.

The composition may be to be administered orally, enterally or parenterally.

In general oral administration is preferred, since it can be easily done at home, and would consequently allow using the subject matter of the present invention in a private atmosphere. Everybody could easily have access to and use the compositions of the present invention, optionally after consultation with medical personnel.

In hospitalized conditions, malnutrition and lack of appetite is often a serious problem that may cause delays in the recovery process. For people not willing to or unable to consume food orally, enteral administration of the compositions of the present invention may be a preferred option, for example as tube feeding formulation.

If oral and/or enteral administration is not possible or not recommended, parenteral administration may be used. Hence, the composition of the present invention may also be in a form suitable for parenteral administration. Such compositions often do not contain a carbohydrate source, for example.

The composition may be to be administered as a meal or in the framework of a meal.

The composition may also to be administered within one hour before or during a meal, for example. As such it may serve as a functional appetizer, for example.

Those skilled in the art will understand that they can freely combine all features of the present invention described herein, without departing from the scope of the invention as disclosed. In particular, features described for the use of the present invention may be applied to the compositions of the present invention and vice versa.

Further advantages and features of the present invention are apparent from the following Examples and Figures.

FIG. 1 summarized the experimental design.

EXAMPLES

A cohort of male Wistar rats born and breed in a non-specific-pathogen-free animal facility (Unité de Nutrition Comparée, INRA Theix) was used for the study. When rats were 18 month old they were weighted monthly to evaluate their body weight change and blood was sampled in order to quantify inflammatory markers (acute phase proteins: α2-macroglobulin and fibrinogen). At the age of 21 months, rats were divided in two groups matched for body weight, body weight loss, and inflammatory status. Rats were fed with supplemented diets, starting at the age of 21 months and for 14 weeks. The cysteine diet consisted in the commercial pelleted diet A04 (SAFE/UAR, Scientific Animal Food and Engineering, Villemoisson-sur-Orge, France) supplemented with 4.0 g of L-cysteine (Sigma) per kg, and the control diet was supplemented with 2.9 g of L-alanine (Jerafrance) per kg (iso-nitrogenous diets). Experimental diets have been prepared at the Unite Préparation Aliments Expérimentaux, INRA Jouy-en-Josas. The amino acid composition of the commercial (non-supplemented) diet is presented in Table 1.

TABLE 1

Amino acid composition of the commercial diet (A04).

| Amino acid | Content in protein (g/100 g) | Content in the commercial diet (g/kg) |
|---|---|---|
| aspartic acid | 7.5 | 12.22 |
| threonine | 3.5 | 5.70 |
| serine | 3.9 | 6.41 |
| glutamate | 20.3 | 33.15 |
| proline | 7.4 | 12.03 |
| glycine | 5.2 | 8.53 |
| alanine | 4.6 | 7.52 |
| valine | 4.3 | 6.98 |
| cysteine | 1.74 | 2.84 |
| methionine | 2.00 | 3.26 |
| isoleucine | 3.4 | 5.58 |
| leucine | 7.1 | 11.61 |
| tyrosine | 3.2 | 5.29 |
| phenylalanine | 4.4 | 7.18 |
| lysine | 4.5 | 7.29 |
| histidine | 2.3 | 3.69 |
| arginine | 5.6 | 9.17 |
| Total | 91.1 | 148.46 |

1—Mortality

Figure 1:
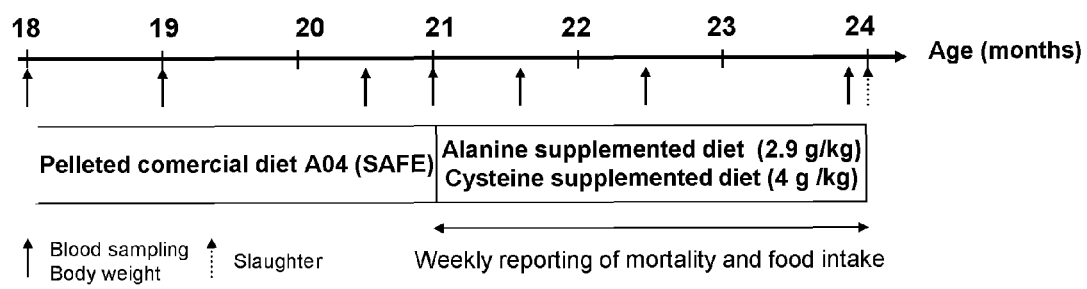
Figure 2:
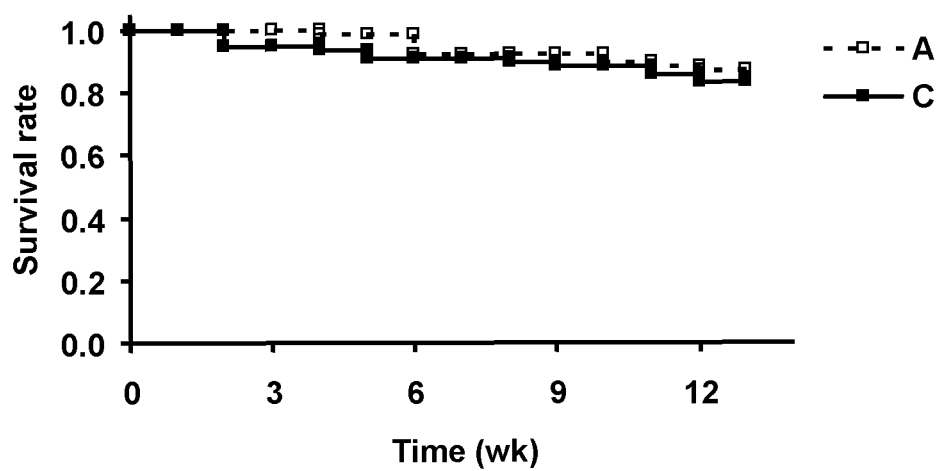
FIG. 2 shows Kaplan-Meier survival curves of old rats fed with an alanine (A) and a cysteine (C) diet. Log-rank test=0.054, P=0.816.

Survival curves were generated by Kaplan-Meier method (FIG. 2) and compared by the log-rank test in order to analyze the effect of cysteine supplementation on mortality.

Cysteine supplementation did not change the mortality rate.

2—Body Weight

Figure 3:
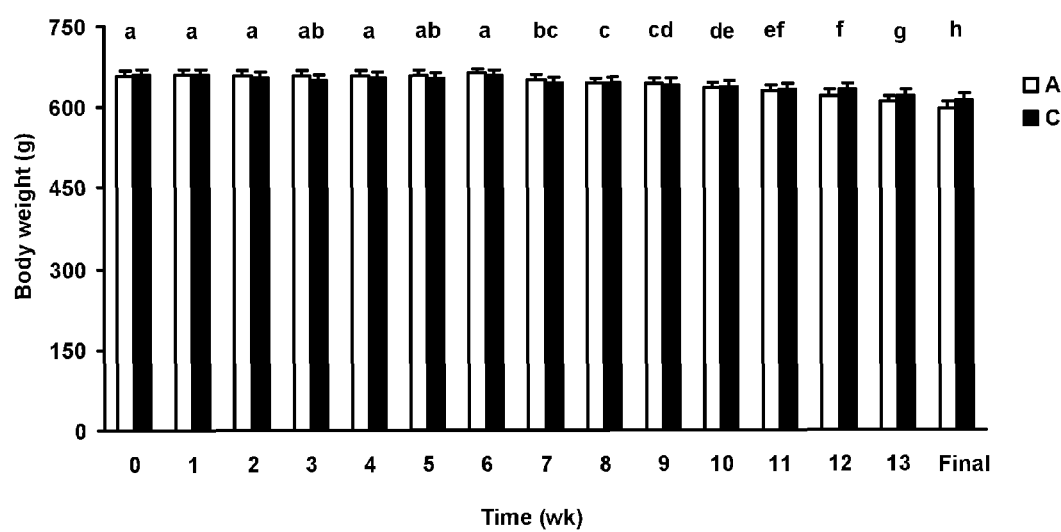
FIG. 3 shows the effect of cysteine supplementation on body weight. Two-way Anova for repeated measurements: Time (T): P<0.0001, Diet (D): P=0.915, T×D: P=0.137. $^{a\ to\ h}$ time points not sharing a common letter are significantly different (Fisher's PLSD, P<0.05).

Body weight (FIG. 3) decreased with time and it became significantly different from the initial value at 7 weeks of supplementation. The decrease accelerated at the end of the experiment since body weights of the two last weeks were different from each of the previous ones.

3—Food Intake

Figure 4:
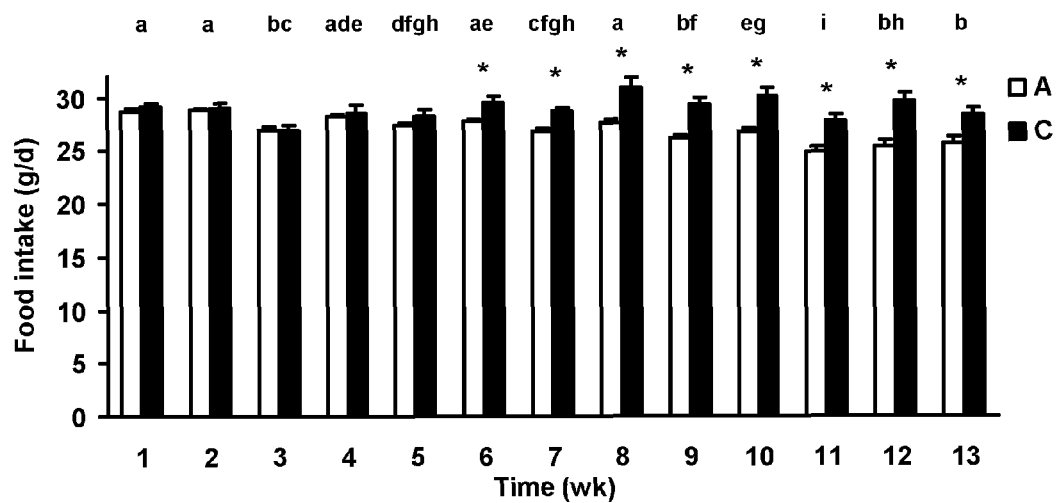
FIG. 4 shows the effect of cysteine supplementation on food intake. Two-way Anova for repeated measurements: Time (T): P<0.0001, Diet (D): P=0.0002, T×D: P<0.0001. $^{a\ to}$ $^{i}$ time points not sharing a common letter are significantly different (Fisher's PLSD, P<0.05).

Food intake (FIG. 4) decreased with time and was lower for the alanine diet. The significant interaction between time and diet reveals that cysteine was able to blunt the decrease in food intake associated with aging. Indeed, food intake significantly decreased by 0.96% per week in the alanine group (significant linear regression r=0.88, P<0.0001) whereas it was unchanged in the cysteine group (r=0.20, P=0.50).

The consumption of the 4 g cysteine supplemented diet blunts the decrease in food intake that occurred when rats were about 22.5 months old suggesting that cysteine exhibit an anti ageing-associated anorexia property.

4—Body Weight, Skeletal Muscle and Organ Weights

As shown in Table 3, cysteine supplemented rats exhibited a higher liver weight than control rats.

TABLE 3

Effect of cysteine supplementation on body, skeletal muscle and organ weights

| Parameter | Diet | |
|---|---|---|
| | Alanine (n = 61) | Cysteine (n = 62) |
| Initial BW (g) | 657 ± 10 | 661 ± 10 |
| Final BW (g) | 595 ± 13 | 613 ± 12 |
| BW change (%/13 wk) | −7.03 ± 1.60 | −6.27 ± 1.18 |
| Gastrocnemius (g) | 2.51 ± 0.04 | 2.51 ± 0.04 |
| Tibialis (mg) | 888 ± 16 | 889 ± 18 |
| EDL (mg) | 222 ± 4 | 228 ± 4 |
| Soleus (mg) | 177 ± 3 | 178 ± 4 |
| Liver (g) | 18.4 ± 0.5 | 20.0 ± 0.4 |
| Small intestine (g) | 11.4 ± 0.3 | 12.0 ± 0.2 |
| Colon (g) | 2.68 ± 0.06 | 2.76 ± 0.07 |
| Kidneys (g) | 4.32 ± 0.19 | 4.31 ± 0.17 |

BW: body weight.

The invention claimed is:

1. A method for the treatment of malnutrition and/or a disorder related thereto in an elderly subject in need thereof, the method comprising administering to the elderly subject a nutritional composition that contains from about 20 to 70% of the calories of the nutritional composition from carbohydrates, and a protein fraction comprising at least 5 weight-% cysteine to increase food intake and/or decrease satiety and/or satiation.

2. The method in accordance with claim 1, wherein the cysteine is provided in a form of a cysteine precursor selected from the group consisting of cysteine bound in a protein, a peptide hydrolysate, a peptide, and mixed disulfides.

3. The method in accordance with claim 1, wherein the nutritional composition comprises the cysteine in an amount of at least 2 g/kg dry weight of the composition.

4. The method in accordance with claim 1, wherein the cysteine increases appetite.

5. The method in accordance with claim 1, wherein the disorder related to malnutrition is selected from the group consisting of anorexia, anorexia nervosa, cachexia, inflammatory diseases associated with decreased food intake, and combinations thereof.

6. The method in accordance with claim 1, wherein the cysteine is chemically pure cysteine.

7. The method in accordance with claim 1, wherein the cysteine treats an age related decrease in food intake.

8. The method in accordance with claim 1, wherein the nutritional composition comprises the cysteine in an amount of at least 10 g/kg dry weight of the composition.

9. The method in accordance with claim 1, wherein the nutritional composition is administered through a route selected from the group consisting of orally, enterally and parenterally, and wherein the nutritional composition is to be administered within one hour before a meal, during a meal, or as replacement of a meal.

10. A nutritional composition comprising at least 5 weight-% of chemically pure cysteine and from about 20 to 70% of the calories of the nutritional composition from carbohydrates.

11. The nutritional composition in accordance with claim 10, wherein the nutritional composition has a caloric density of at least 0.5 kcal/g.

12. The nutritional composition in accordance with claim 10, wherein the nutritional composition comprises about 10 to 40% of the calories of the nutritional composition from proteins.

13. The nutritional composition in accordance with claim 10, wherein the nutritional composition comprises about 15 to 45% of the calories of the nutritional composition from lipids.

14. The nutritional composition in accordance with claim 10, wherein the nutritional composition is selected from the group consisting of a food product, a pet food product, a drink, a pharmaceutical, a nutritional formula, a composition for clinical nutrition, a nutritional powder to be reconstituted by addition of water, a juice or milk, a nutraceutical, a food additive, a food supplement, a dairy product, and a gel.

15. A method for the prevention of malnutrition comprising the step of administering to an elderly subject a nutritional composition that contains from about 20 to 70% of the calories of the nutritional composition from carbohydrates and a protein fraction comprising at least 5 weight-% cysteine to increase food intake and/or decrease satiety and/or satiation.

16. The method in accordance with claim 15, wherein the cysteine is provided in a form of a cysteine precursor selected from the group consisting of cysteine bound in a protein, a peptide hydrolysate, a peptide, and mixed disulfides.

17. The method in accordance with claim 15, wherein the nutritional composition comprises the cysteine in an amount of at least 2 g/kg dry weight of the composition.

18. The method in accordance with claim 15, wherein the cysteine increases appetite.

19. The method in accordance with claim 15, wherein the cysteine is chemically pure cysteine.

20. The method in accordance with claim 15, wherein the cysteine treats an age related decrease in food intake.

21. The method in accordance with claim 15, wherein the nutritional composition comprises the cysteine in an amount of at least 10 g/kg dry weight of the composition.

22. The method in accordance with claim 1, wherein the cysteine is provided in a form selected from the group consisting of gamma-glutamyl-cysteine, L-cysteine-glutathione cysteine prodrugs, N-acetyl-cysteine (free form, amide or ester forms), S-allyl-cysteine, S-methyl-cysteine, S-ethyl-cysteine, S-propyl-cysteine, TCA (thiazelidineScarboxylic acid), OTC (L-2-Oxothiazolidine-4-carboxylate), and S-hydroxy-methyl mercapto L-cysteine.

23. The method in accordance with claim 15, wherein the cysteine is provided in a form selected from the group consisting of gamma-glutamyl-cysteine, L-cysteine-glutathione cysteine prodrugs, N-acetyl-cysteine (free form, amide or ester forms), S-allyl-cysteine, S-methyl-cysteine, S-ethyl-cysteine, S-propyl-cysteine, TCA (thiazelidineScarboxylic acid), OTC (L-2-Oxothiazolidine-4-carboxylate), and S-hydroxy-methyl mercapto L-cysteine.

24. The method in accordance with claim 1, wherein the cysteine is administered in a daily dose of about 0.03 to 0.15 g/kg body weight.

25. The method in accordance with claim 15, wherein the cysteine is administered in a daily dose of about 0.03 to 0.15 g/kg body weight.

26. The method in accordance with claim 1, wherein the protein fraction comprises at least 10 weight-% cysteine.

27. The method in accordance with claim 15, wherein the protein fraction comprises at least 10 weight-% cysteine.

* * * * *